US009034380B2

(12) United States Patent
Rademacher et al.

(10) Patent No.: US 9,034,380 B2
(45) Date of Patent: May 19, 2015

(54) NANOPARTICLES COMPRISING ANTIBACTERIAL LIGANDS

(75) Inventors: Thomas William Rademacher, Oxford (GB); Godfrey Bradman, Oxford (GB); Soledad Penades Ullate, Madrid (ES); Rafael Ojeda Martinez De Castilla, Madrid (ES)

(73) Assignee: Midatech Ltd., Abingdon, Oxford, Oxfordshire (GB)

( * ) Notice: Subject to any disclaimer, the term of this patent is extended or adjusted under 35 U.S.C. 154(b) by 1177 days.

(21) Appl. No.: 11/997,816

(22) PCT Filed: Aug. 4, 2006

(86) PCT No.: PCT/GB2006/002923
§ 371 (c)(1),
(2), (4) Date: Nov. 5, 2008

(87) PCT Pub. No.: WO2007/015105
PCT Pub. Date: Feb. 8, 2007

(65) Prior Publication Data
US 2009/0181101 A1    Jul. 16, 2009

Related U.S. Application Data

(60) Provisional application No. 60/705,175, filed on Aug. 4, 2005.

(30) Foreign Application Priority Data

Aug. 4, 2005 (GB) .................................. 0516070.0

(51) Int. Cl.
*A61K 47/48* (2006.01)
*A61K 41/00* (2006.01)
*B82Y 5/00* (2011.01)

(52) U.S. Cl.
CPC ........ *A61K 47/48861* (2013.01); *Y10S 977/773* (2013.01); *Y10S 977/906* (2013.01); *A61K 41/0052* (2013.01); *A61K 47/48115* (2013.01); *A61K 47/48884* (2013.01); *B82Y 5/00* (2013.01)

(58) Field of Classification Search
None
See application file for complete search history.

(56) References Cited

U.S. PATENT DOCUMENTS

| 5,776,712 A * | 7/1998 | Kuusela et al. ............... 435/7.33 |
| 2003/0236443 A1 * | 12/2003 | Cespedes et al. ............... 600/29 |
| 2004/0052729 A1 * | 3/2004 | Penades et al. ............... 424/1.73 |
| 2006/0057631 A1 | 3/2006 | Zou et al. |
| 2008/0268061 A1 | 10/2008 | Jordan et al. |

FOREIGN PATENT DOCUMENTS

| EP | 1 624 306 A1 | 2/2006 | |
| WO | 02/32404 A2 | 4/2002 | |
| WO | 03/022999 A2 | 3/2003 | |
| WO | 2004/108165 A2 | 12/2004 | |
| WO | WO 2004108165 A2 * | 12/2004 | ............. A61K 47/48 |
| WO | 2005/044365 A2 | 5/2005 | |
| WO | 2006/037979 A2 | 4/2006 | |
| WO | WO 2006037979 A2 * | 4/2006 | |

OTHER PUBLICATIONS

H Gu, P-L Ho, KWT Tsang, C-W Yu, B Xu. "Using Biofunctional Magnetic Nanoparticles to Capture Gram-Negative Bacteria at an Ultra-Low Concentration." Chem Commun, 2003, pp. 1966-1967.*
H Gu, PL Ho, E Tong, L Wang, B Xu. "Presenting Vancomycin on Nanoparticles to Enhance Antimicrobial Activities." Nano Letters, vol. 3 No. 9, 2003, pp. 1261-1263.*
J Lin, W Zhou, A Kumbhar, J Wiemann, J Fang, EE Carpenter, CJ O'Connor. "Gold-Coated Iron (Fe@Au) Nanoparticles: Synthesis, Characterization, and Magnetic Field-Induced Self-Assembly." Journal of Solid State Chemistry, vol. 159, 2001, pp. 26-31.*
RT Tom, V Suryanarayanan, PG Reddy, S Baskaran, T Pradeep. "Ciprofloxacin-Protected Gold Nanoparticles." Langmuir, vol. 20, 2004, pp. 1909-1914.*
J Fink, CJ Kiely, D Bethell, DJ Schiffrin. "Self-Organization of Nanosized Gold Particles." Chem. Mater., vol. 10, 1998, pp. 922-926.*
De La Fuente, Jesus M. et al. "Understanding carbohydrate-carbohydrate Interactions by means of glyconanotechnology", Glycoconjugate Journal, 21: 149-163 (2004).
Grace, A. Nirmala et al., "Antibacterial efficacy of aminoglycosidic antibiotics protected gold nanoparticles—A brief study", Colloids and Surfaces: A Physicochem. Eng. Aspects, 297: 63-70 (2007).
Gu, Hongwei al., "Using biofunctional magnetic nanoparticles to capture Gram-negative bacteria at an ultra-low concentration", Chemical Communications, 15: 1966-1967 (2003).
Gu, Hongwei et al., "Presenting Vancomycin on Nanoparticles to Enhance Antimicrobial Activities", Nano Letters, 3(9): 1261-1963 (2003).
Jensen, Katie L. et al., "Use of Gold Nanoparticles to Identify Targets of Membrane-Active Steroid Antibiotics", Abstracts of Papers American Chemical Society, 223, p. CHED 855 (2002).
Lin, Chun-Cheng et al., Selective Binding of Mannose-Encapsulated Gold Nanoparticles to Type 1 Pili in *Escherichia coli*, J. Am. Chem. Soc., 124: 3508-3509 (2002).
Lin, Ya-Shivan et al., "Affinity Capture Using Vancomycin-Bound Magnetic Nanoparticles of the MALDI-MS Analysis of Bacteria", Anal. Chem., 77: 1753-1760 (2005).
Naruse, Yujiro, "Theoretical Concept of Physical Antibiotics Using Nanoparticles", The Japan Society of Applied Physics, 44: 3330-3332 (2005).

(Continued)

*Primary Examiner* — Frederick Krass
*Assistant Examiner* — Isaac Shomer
(74) *Attorney, Agent, or Firm* — Patrick J. Hagan; Dann, Dorfman, Herrell and Skillman, P.C.

(57) ABSTRACT

Materials and Methods are disclosed for producing nanoparticles linked to antibacterial ligands, including antibiotics and/or molecules which bind to bacterial markers, and for the use of the nanoparticles for the treatment of conditions treatable by the antibiotic ligands.

20 Claims, 8 Drawing Sheets

(56) References Cited

OTHER PUBLICATIONS

Ramakrishnan, Ramesh et al., "Sensitive Assay for Identification of Methicillin-Resistant *Staphylococcus aureus*, Based on Direct Detection of Genomic DNA by Use of Gold Nanoparticle Probes", Clinical Chemistry, 50(10): 1949-1952 (2004).

Storhoff, James L., "One-Pot Calorimetric Differentiation of Polynucleotides with Single Base Imperfections Using Gold Nanoparticle Probes", J. Am. Chem. Soc., 120: 1959-1964 (1998).

Sun, Shouheng et al., "Monodisperse FePt Nanoparticles and Ferromagnetic FePt Nanocrystal Superlattices", Science, 287: 1989-1992 (2000).

Tom, Renjis T. et al., "Ciproflaxocin-Protected Gold Nanoparticles", Langmuir, 20: 1909-1914 (2004).

Zharov, Vladimir et al., "Photothermal guidance for selective photothermolysis with nanoparticles", Proc. of SPIE, 5319: 291-300 (2004).

Lin, Chun-Cheng et al., "Detailed experimental procedures, stability measurements, competition assays and data analyses for UV-vis, TEM, XPS, IR and NMR spectroscopy", J. Am. Chem. Soc., 24(14): 1-7 (2002).

* cited by examiner

Fig. 1

Glyconanoparticle
Glucose/Amoxycillin + Polymixin B

NANOPARTICLES COMPRISING ANTIBACTERIAL LIGANDS

CROSS-REFERENCE TO RELATED APPLICATIONS

This application is the U.S. National Stage of International Application No. PCT/GB2006/002923, filed Aug. 4, 2006, which claims priority from U.S. Provisional Application No. 60/705,175, filed Aug. 4, 2005 and Great Britain Application No. 0516070.0, filed Aug. 4, 2005. The entire disclosure of each of the aforesaid applications is incorporated by reference in the present application.

FIELD OF THE INVENTION

The present invention relates to nanoparticles, and more particularly to nanoparticles comprising antibacterial substances such as antibiotics. The invention further relates to uses of the nanoparticles, in particular in treating bacterial infections.

BACKGROUND OF THE INVENTION

Our ability to treat infectious diseases came from the introduction of penicillin 60 years ago. Whilst still a front-line drug for some infections, several pathogenic bacteria have now developed penicillin resistance. As early as the late 1950's Staphylococcus aureus was developing resistance to benzyl-penicillin due to the production of β-lactamase, an enzyme capable of degrading penicillin (reviewed in Stapleton and Taylor (2002) Sci. prog. 85, 57-72). Methicillin, a disubstituted derivative of penicillin, was developed to overcome this resistance. Unfortunately, within the same year that methicillin was used clinically, methicillin resistant S. aureus (MRSA) strains were already detected. Resistance was not due to lactamase production, but to the additional production of a penicillin-binding protein (PBP2α) acquired from another species (Chambers (1997) Clin. Microbil. Rev. 10, 781-791). PBP's are a family of enzymes responsible for cross-linking the glycan chains of the cell wall and are crucial in maintaining bacterial survival.

The over prescription and excessive use of different antibiotics over years has now led to multi drug-resistant MRSA strains. These pose a serious health problem particularly in the USA and Europe. A less publicized area of concern is the irresponsible application of antibiotics for non-human use such as in agriculture and veterinary practice. This has accelerated the development of resistance that can be transferred to human pathogens by plasmids. The cheaply manufactured tetracyclines, in particular, have often been used at sub-therapeutic doses as growth promoters for chickens, pigs and cattle. This practice was banned in Europe in the early 1970's but is still used in the USA and Australia. In 1995, over 3,000 tonnes of tetracyclines were used in the USA alone as animal feed supplements. Human usage was just a few tonnes. Considerable evidence exists suggesting that the use of antibiotics in farm animals has led to resistance development (reviewed in Chopra and Roberts (2001) Microbiol. Mol. Biol. Rev. 655, 232-260).

In the February 2000 report, the National Audit Office noted that hospital-acquired infections (nosocomial) were each year costing the NHS around £1 billion and resulting in at least 5,000 deaths. In the USA alone MRSA costs for 1993 were in excess of $7 billion.

Hospital-acquired infections are now being pursued on several fronts. These range from the practical issues within hospitals such as tackling the factors which inhibit good practice, a more robust approach to antibiotic prescribing, hospital hygiene in general and instituting a system of mandatory surveillance. Therapeutic options are also being investigated. These include production of new structural variants of existing antibiotic classes but with obvious testing against MRSA, combination therapies for example antibiotic with a specific inhibitor that protects the antibiotic from inactivation or removal from the cell (antibiotic efflux is now recognised as a major mechanism of bacterial antibiotic resistance), re-evaluation of earlier pharmacophores and discovery or design of new agents.

Other problems which may be encountered in the use of antibiotics include hypersensitivity reactions and toxicity. Synergistic toxicity may arises when two or more antibiotics are used together, e.g. use of vancomycin and aminoglycoside may lead to renal toxicity.

New methods of combatting bacterial infection are constantly being sought, in improvements in use of current antibiotics and in alternatives to traditional antibiotic technology.

SUMMARY OF THE INVENTION

Broadly, the present invention provides materials and methods for producing nanoparticles linked to antibacterial ligands. Suitable antibacterial ligands include antibiotics and molecules which bind to bacterial markers. These ligands or further ligands linked to the cores of the nanoparticles may further comprise carbohydrate groups, peptides, protein domains, nucleic acid segments or fluorescent groups. These nanoparticles can then be used to target bacterial cells. In some embodiments, the particles have the further advantage that they are soluble, e.g. in water and a range of organic solvents, and can be used in a variety of homogeneous application formats. In preferred embodiments, the nanoparticles are magnetic.

The present invention enables delivery of antibiotics to be combined with bacterial cell killing by hyperthermia or magnetocytolysis, by exposing the nanoparticles to a magnetic field or infra-red light. Alternatively, hyperthermia or magnetocytolysis alone may be used.

Accordingly, in a first aspect, the present invention provides a nanoparticle which comprises a core including metal atoms, which core is covalently linked to a plurality of ligands which comprise at least one antibacterial ligand. In a preferred embodiment, the core is a magnetic core.

In certain embodiments, at least one of the ligands is attached to the nanoparticle via a linker group. The linker group may comprise, for example, a thiol group, an alkyl group, a glycol group or a peptide group. In preferred embodiments the linker group comprises C2-C15 alkyl and/or C2-C15 glycol.

In one embodiment, the antibacterial ligands comprise antibiotics such as pencillins (including methicillin and amoxicillin), tetracyclines, polymyxin B, quinolones such as Ciprofloxacin, cephalosporins, rifampicin, and glycopeptide antibiotics such as vancomycin and teicoplanin. In some embodiments, the ligands comprise more than one antibiotic.

Additionally or alternatively, the antibacterial ligands may comprise moieties that bind bacterial markers. Suitable bacterial markers include carbohydrate an cell wall markers such as polysaccharides, lipopolysaccharide, glycans and peptidoglycans. For example, antibacterial antibodies or lectins may be used.

Apart from these components described above, it may also be useful to include further ligands to shield other elements of the nanoparticle from recognition in vivo. Most conveniently, this can be accomplished by including a carbohydrate ligands, e.g. the glucose ligands of the type discussed above.

In addition to the ligands described above, the nanoparticles may comprise one or more further types of ligands. For example, the additional ligands, or groups or domains of ligands, may include one or more peptides, a protein domain, a nucleic acid molecule, a lipidic group, a carbohydrate group, any organic or anionic or cationic group, a glycolipid or a glycoprotein. The carbohydrate group may be a polysaccharide, an oligosaccharide or a monosaccharide group (e.g. glucose). Preferred ligands include glycoconjugates, thereby forming glyconanoparticles.

In preferred embodiments, the nanoparticle core comprises Au and/or Fe. The core may consist of a single metal e.g. Au, Ag, Pt, Pd, Fe or Co, or may be an alloy, for example an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd. In other embodiments, the core may comprise a metal oxide e.g. iron oxide.

In a further aspect, the present invention provides a nanoparticle comprising antibacterial ligands as defined above which has a magnetic core.

Preferably, the magnetic core comprises passive metal atoms and magnetic metal atoms, and the ratio of passive metal atoms to magnetic metal atoms in the core is between about 5:0 and about 2:5. More preferably, the ratio is between about 5:0 and about 5:1.

In preferred embodiments, the mean diameter of the core, preferably the metallic core, is between 0.5 and 100 nm, more preferably between 1 and 50 nm, more preferably between 1 and 20 nm. Still more preferably, the mean diameter of the core is below 2 nm. When the ligands are considered in addition to the cores, preferably the overall mean diameter of the particles is between 5.0 and 100 nm, more preferably between 5 and 50 nm and most preferably between 10 and 30 nm. The mean diameter can be measured using techniques well known in the art such as transmission electron microscopy.

In a preferred embodiment the diameter of the nanoparticles (core plus ligands) are between 1 and 20 nm in diameter, more preferably approximately 1-3 nm in diameter. This may be particularly advantageous when targetting bacteria with their smaller size (approx 1 μm diameter) compared to mammalian cells (approx 10 μm diameter), in that a more complete or densely packed layer of nanoparticles could be achieved round the bacteria.

In another aspect, the present invention provides compositions comprising populations of one or more of the above defined particles. In some embodiments, the populations of nanoparticles may have different densities of the same or different ligands attached to the core.

In a further aspect, the present invention provides a method of producing a nanoparticle as described herein. Conveniently, the method comprises conjugating the antibacterial ligand to the core of the nanoparticle by derivatising the antibacterial ligand with a linker and including the derivatised ligand in a reaction mixture from which the core of the nanoparticle is synthesised. For example, to produce ligand-conjugated gold nanoparticles, a methanolic solution of the derivatised ligand may be added to an aqueous solution of $HAuCl_4$ and the resulting mixture reduced with $NaBH_4$. During self-assembly of the nanoparticles, the nanoparticle cores attach to the antibacterial via the linker.

In one embodiment, the linker is a disulphide linker, for example a mixed disulphide linker, although ethylene linkers or peptide linkers may also be employed. An exemplary linker group is represented by the general formula $HO—(CH_2)_n—$ $S—S—(CH_2)_m—OH$, wherein n and m are independently between 1 and 5. The RNA can conveniently be linked to the spacer via a terminal phosphate group, and in the case of the preferred mixed disulphide linkers via one of the terminal hydroxyl groups. When the nanoparticles are synthesized, the —S—S— of the linker splits to form two thio linkers that can each covalently attach to the core of the nanoparticle via a —S— group. The use of mixed disulphide linker helps to avoid the formation of RNA dimers. The linker may also comprise, for example, a thiol group, an alkyl group, a glycol group or a peptide group. In preferred embodiments the linker group comprises C2-C15 alkyl and/or C2-C15 glycol In some embodiments, the nanoparticle of the present invention comprises a detectable label. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5. Magnetic labels include paramagnetic groups comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ or lanthanides$^{3+}$.

In some embodiments, the nanoparticles may comprise a radionuclide for use in detecting the nanoparticle using the radioactivity emitted by the radionuclide, or for therapy, i.e. for killing target cells The present invention provides a way of presenting a spherical array of ligands having advantages over other types of array proposed in the prior art. In particular, the nanoparticles are soluble in most organic solvents and especially water. This can be used in their purification and importantly means that they can be used in solution for presenting the ligand immobilised on the surface of the particle. The fact that the nanoparticles are soluble has the advantage of presenting the ligands in a natural conformation. For therapeutic applications, the nanoparticles are non toxic, soluble and stable under physiological conditions.

In a further aspect, the present invention provides compositions comprising populations of one or more of the above defined particles. In some embodiments, the populations of nanoparticles may have different densities of the same or different ligands attached to the core. In some cases, it may be desirable to encapsulate the nanoparticles to enable the delivery of a plurality of nanoparticles to a target site. Suitable encapsulation technologies are well known the those skilled in the art. The encapsulated population of nanoparticles may be of one, two, three or a plurality of different types. In one embodiment, the present invention provides an aerosol composition of nanoparticles as defined herein. The aerosol composition may comprise the nanoparticles and optionally a diluent. Examples of the uses of these compositions are discussed below. In preferred embodiments, the composition comprises a pharmaceutically acceptable carrier.

In a further aspect, the present invention provides a method of medical treatment comprising administering a pharmaceutically effective amount of the nanoparticles described above to a human or animal subject. In some embodiments, the method further comprises exposing the patient to infrared light or to a DC or AC magnetic field, or a radio frequency magnetic field induced by inductive coupling.

In a further aspect, the present invention provides the above defined nanoparticles for use in therapy or diagnosis.

The invention also provides the use of the above defined nanoparticles for the preparation of a medicament for the treatment of a bacterial or fungal infection. Examples of specific uses that may be treated according to the present invention are described below, along with other applications of the nanoparticles, both in vitro and in vivo uses. For example, the nanoparticles described herein or their derivatives can be formulated in pharmaceutical compositions, and administered to patients in a variety of forms, in particular to treat bacterial or fungal infections.

In one embodiment, magnetic nanoparticles and ferrofluids of the invention can be used to treat bacterial infection by hyperthermia. The nanoparticles are targeted to bacterial cells by the antibacterial and then subjected to a high frequency AC magnetic field.

In another embodiment, magnetic nanoparticles of the invention can be used to treat bacterial infections by magnetocytolysis of bacterial cells. The nanoparticles are targeted to bacterial cells by the antibacterial and then subjected to a DC magnetic field.

Nanoparticles, such as those having cores comprising Au atoms, can also be heated using inductive coupling using 1-2 GHz. The heat thus generated by the relaxation magnetic energy of the magnetic material kills the bacterial cells to which the nanoparticles are attached.

Alternatively, near IR (infra-red) light may be used. Exposing nanoparticles to IR radiation at a frequency that is absorbed by the nanoparticles, but not by the tissues of the body, enables selective destruction of the cells to which the nanoparticles are bound.

Additionally or alternatively, the nanoparticles may be used to deliver antibiotics to bacterial or fungal cells. Delivery of antibiotic may be combined with or followed by magnetolytic or hyperthermic therapy as described above.

Embodiments of the present invention will now be described by way of example and not limitation with reference to the accompanying figures.

DETAILED DESCRIPTION

Metallic Core

The core material may be formed of one or more than one type of metal atom (e.g. Au, or another passive metal atom). In some embodiments, the core material is a composite or an alloy of a passive metal and a magnetic metal. Preferred passive metals are Au, Ag, Pt, Pd or Cu and preferred magnetic metals are Fe and Co, with the most preferred composite being Au/Fe. Other composites or alloys may also be used. Nanoparticle cores may also be formed from alloys including Au/Fe, Au/Cu, Au/Gd, Au/Zn, Au/Fe/Cu, Au/Fe/Gd and Au/Fe/Cu/Gd, and may be used in the present invention. Preferred core materials are Au and Fe, with the most preferred material being Au.

The cores of the nanoparticles preferably comprise between 100 and 500 atoms (e.g. gold atoms), more preferably between about 20 and 500 atoms, and still more preferably between about 50 and 500 atoms, to provide core diameters in the nanometer range. A further example of nanoparticles of the present invention have cores formed from Au atoms and Gd, e.g. Gd III, e.g. having a mean diameter less than 10 nm, more preferably less than 5 nm and most preferably about 2.5 nm. Preferred particles of this type comprise between about 1-20% Gd atoms and 99 to 80% Au atoms, and more preferably between about 1-10% Gd and 99 to 90% Au, based on the ratio of the ratio of respective metal atoms present in the core of the nanoparticle.

Magnetic nanoparticles may also be formed from materials such as MnFe (spinel ferrite) or CoFe (cobalt ferrite) with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, magnetic nanoparticles may have cores composed of passive metals which are not magnetic as single atoms, such as Au or Pd. The inventors have found that when very small nanoparticles are made from such metals they may exhibit ferromagnetic properties, in particular when conjugated to ligands (see Sampedro et al. 2003, Phys. Rev. Letts. 91(23) 1-4; Crespo P et al 2004. Physical Rev Lett 93; 087204). The magnetic properties of the nanoparticles are a result of the interplay between the size effect and the ligand effect so can be tuned by altering the size of the nanoparticles and the ligands to which they are conjugated.

Thus, thiol capped Au based nanoparticles which possess superparamagnetism/ferromagnetism (Crespo P et al 2004. Physical Rev Lett 93; 087204) may be used as magnetic nanoparticles to which antibacterial ligands may be conjugated.

As used herein, the term 'passive metals' refers to metals which do not show magnetic properties as lone atoms and are chemically stable to oxidation.

The passive metals of the invention may be diamagnetic. 'Diamagnetic' refers to materials with all paired electrons which thus have no permanent net magnetic moment per atom. 'Magnetic' materials have some unpaired electrons and are positively susceptible to external magnetic fields—that is, the external magnetic field induces the electrons to line up with the applied field, so the magnetic moments of the electrons are aligned.

Magnetic materials may be paramagnetic, superparamagnetic or ferromagnetic. Paramagnetic materials are not very susceptible to external magnetic fields and do not retain their magnetic properties when the external magnetic field is removed. Ferromagnetic materials are highly susceptible to external magnetic fields and contain magnetic domains even when no external magnetic field is present, because neighbouring atoms cooperate so their electron spins are parallel. External magnetic fields align the magnetic moments of neighbouring domains, magnifying the magnetic affect. Very small particles of materials that normally have ferromagnetic properties are not ferromagnetic, as the cooperative effect does not occur in particles of 300 nm or less so the material has no permanent magnetism. However, the particles are still very susceptible to external magnetic fields and have strong paramagnetic properties, and are known as superparamagnetic. Preferably, the nanoparticles of the invention are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and $lanthanides^{+3}$.

Ligand

Antibacterial Ligand

Antibacterial ligands may be, for example, antibiotics. Antibiotics are compounds which slow the growth of or kill bacterial cells. Additionally or alternatively, the antibacterial ligands may be molecules which bind bacterial markers.

Suitable antibiotics include:

1. A range of pencillins (including methicillin, ampicillin and amoxycillin), which may bind the cell wall PRP (penicillinase resistant penicillins) giving selectivity of binding bacteria versus host tissue. Penicillins will be of potential use against Gram positive bacteria such as MRSA (*Staphylococcus aureus*).

2. Cephalosporins also interfere with synthesis of the bacterial cell wall. They include cephamycin, cefonicid, cefotetan and cephalothin.

3. Tetracyclines, including chlortetracycline, exytetracycline and doxycycline, which inhibit bacterial protein synthesis by preventing the association of aminoacyl-tRNA with bacterial ribosomes. It is believed that they bind the 30S ribosomal subunit although there is some controversy regarding the exact binding site. Tetracyclines are broad spectrum agents being active against not only Gram positive and negative bacteria but also mycoplasmas and various protozoans including *Plasmodium* (the pathogen which causes malaria).

4. Aminoglycosides also bind to the 30S subunit of the bacterial ribosome. They include streptomycin, kanamycin, neomycin and gentamycin. Aminocyclitols such as spectinomycin work the same way.

5. Macrolides, lincosamides and streptogramins bind to the 23 subunit of the bacterial ribosome. They include erythromycinm azithromycin, clarithromycin, clindamycin, quinuprstin and dalfopristin.

6. Polymyxins such as polymyxin B. Polymyxin B is a cyclic decapeptide antibiotic. It kills bacteria by binding/disrupting the cell membrane of gram negative bacteria via the lipid A portion of bacterial LPS. Clinically it has uses when applied topically, but it is nephrotoxic and not given systemically. Surprisingly polymyxin B has been shown to be highly effective against skin MRSA (gram +ve) infections, being more potent than vancomycin or gentamicin. (Yoshida and Hiramatsu (1993) Microbiol. Immunol. 37, 853-859). It is also possible that the toxicity of polymyxin B attached to GNPs could be considerably different to the free molecule, due to a combination of the coupling chemistry and possibly lower effective doses due to their effective multivalancy.

7. Quinolones, these interfere with the enzyme DNA gyrase which is essential for duplication of bacterial DNA, e.g. Ciprofloxacin, levofloxacin and moxifloxacin.

8. Glycopeptide antibacterials such as vancomycin and teicoplanin are currently used to treat MRSA. They inhibit cell-wall synthesis.

9. Sulfa drugs such as sulfanilamide and sulfamethoxazole block bacterial folic acid synthesis.

In some embodiments, more than one type of antibiotic may be conjugated to a single nanoparticle. Combination of antibiotics may reduce the possibility of bacterial resistance of antibiotic toxicity developing. Suitable combinations include vancomycin and rifampicin (e.g. for treatment of MRSA), and trimethoprin, sulfamethoxizole and pentamidine (e.g. for treatment of pneumonia caused by *Pneumocystis carinii*).

Additionally or alternatively, the antibacterial ligands may comprise moieties that bind bacterial markers in order to target the nanoparticles to bacterial cells. Suitable bacterial markers include carbohydrate and cell wall markers such as polysaccharides, lipopolysaccharide, glycans and peptidoglycans. For example, antibacterial antibodies or lectins may be used.

Other Ligands

In addition to the antibacterial ligand, the nanoparticles may comprise one or more further types of ligands. For example, the additional ligands may include one or more peptides, a protein domain, a nucleic acid molecule, a lipidic group, a carbohydrate group, any organic or anionic or cationic group. The carbohydrate group may be a polysaccharide, an oligosaccharide or a monosaccharide group. Preferred ligands include glycoconjugates, thereby forming glyconanoparticles. Where a nucleic acid molecule is present), the nucleic acid molecule may comprise single or double stranded DNA or RNA. The particles may have more than one species of ligand immobilised thereon, e.g. 2, 3, 4, 5, 10, 20 or 100 different ligands. Alternatively or additionally, a plurality of different types of nanoparticles may be employed together. In preferred embodiments, the mean number of total ligands linked to an individual metallic core of the particle is at least one ligand, more preferably 50 ligands, more preferably 60 ligands, more preferably at least 80 ligands, and most preferably at least 90 ligands.

The ligand linked to the core may comprise one or more carbohydrate (saccharide) groups, e.g. it may comprise a polysaccharide, an oligosaccharide or a single saccharide group. The ligand may be also be a glycanoconjugate such as a glycolipid or a glycoprotein. In addition to the carbohydrate group, the ligand may additionally comprise one or more of a peptide group, a protein domain, a nucleic acid molecule (e.g. a DNA segment) and/or a fluorescent probe.

In another embodiment, the ligand may be a peptide or a protein. These may be peptides which binds to receptors on a cell, or they may be antibodies, or therapeutic proteins. For example, the ligand may comprise a membrane translocation signal to aid the nanoparticles in permeating through the cell membrane.

Label

In some embodiments, the nanoparticle of the present invention comprises a detectable label. The label may be an element of the core of the nanoparticle or the antibacterial ligand or another ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Treatment

It will be understood that where treatment of bacterial infection is concerned, treatment includes any measure taken by the physician to alleviate the effect of the infection on a patient. Thus, although complete elimination of the infection is a desirable goal, effective treatment will also include any measures capable of achieving reduction of bacterial growth or relieving the symptoms of the disease.

Bacterial diseases which may be treated using the nanoparticles described herein include pneumonia, tuberculosis, cholera, diphtheria, tetanus, diarrhoea, meningitis, botulism, dysentery, typhoid, and diseases resulting from infection by *Staphylococcus* (including MRSA), *Streptococcus, Salmonella, Shigella, Campylobacter, Listeria, Cryptococcus* spp. Some fungal infections such as those caused by *Pneumocystis carinii* may also be treated using antibiotic drugs.

In addition to hyperthermia and magnetocytolysis as described herein, other novel therapeutic possibilities may be viable with antibiotic coated nanoparticles.
1. The use of nanoparticles may allow higher doses of antibiotic to be safely administered.
2. Selective coupling of antibacterials to the nanoparticles may affording protection from degradation leading to higher efficacy.
3. Conjugating multiple antibacterials to the nanoparticles may allow selective targetting of high doses of, for example, tetracyclines to microbes when used in conjunction with polymyxin.
4. The use of spacers and linkers offers potential for different therapeutic opportunities.
5. Nanoparticles with single or mixed antibacterial ligands that bind surface structures of bacteria may provide multivalent binding opportunities, resulting in a high density of nanoparticles, which could enable a lower does of antibiotic to be administered.

Hyperthermia and Magnetolysis

In one embodiment, the nanoparticles and ferrofluids of the invention can be used to treat bacterial infection by hyperthermia or magnetocytolysis. The nanoparticles are targeted to bacterial cells by the antibacterial and then subjected to a magnetic field or infrared radiation as appropriate.

Nanoparticles conjugated to antibacterial ligands may be targeted to bacteria by the antibacterial ligand. The nanoparticles will coat bacteria or may become internalised. They may then be exposed to infrared radiation or, where magnetic nanoparticles are used, subjected to a magnetic field. This causes the nanoparticles to generate heat. If the magnetic field is strong enough and the nanoparticles dense enough, the heat generated will kill the bacteria by localised hyperthermia.

Preferably, an alternating magnetic field is used. Heat is generated by magnetic particles under an alternating magnetic field by hysteresis loss.

Au nanoparticles can also be heated using inductive coupling using 1-2 GHz RFMF (radio-frequency magnetic field).

Inductive coupling is the transfer of energy from one circuit component to another through a shared magnetic field. A change in current flow through one device induces current flow in the other device. The two devices may be physically contained in a single unit, as in the primary and secondary sides of a transformer, or may be separated as in the antennae on a transmitter and a receiver. For an example of the use of inductive coupling to generate a magnetic field for specific heating of gold nanoparticles see Hamad-Schifferli et al (2002) Nature, 415, 152-155.

A similar approach has been successfully tested to kill various tumours in both in vitro and in vivo test models (see Gupta and Gupta (2005) Biomaterials 26, 3995-4021). All the previous approaches tend to use relatively large (5-50 nm) iron oxide ($Fe_3O_4$ and $Fe_2O_3$) based nanoparticles. They show good destruction of cancer cells that are killed when temperatures are raised above 43° C. However, targetting of nanoparticles to cancerous tissue in vivo is problematic, the most common method being direct injection of GNPs into tumours.

For a given excitation frequency, there exists an optimum nanoparticle size that yields a maximum specific absorption rate (SAR) and thus most efficient heating. This technique thus requires nanoparticles with a narrow core size distribution, to maximise the efficiency of the therapy and minimise the amount of ferrofluid to be administered. The nanoparticles of the invention are thus particularly well suited to this application, as the synthesis method enables the size of the nanoparticles to be closely controlled.

In another embodiment, IR (infra-red) light is used to generate hyperthermia. Preferably, infrared radiation at a narrow band of electromagnetic frequencies is used. Near IR light is optimal for such uses because it is not absorbed by cells and is thus most easily transmitted through body tissues. The near IR band contains energy in the range of wavelengths closest to visible light, from approximately 750 nm to approximately 1300 nm. The dimensions of the nanoparticles can be adjusted to absorb a particular infrared radiation frequency. Using a frequency of infrared radiation that is absorbed by the nanoparticles, but not by the tissues of the body, enables the infrared light to pass through the body tissues to be absorbed by the nanoparticles. This causes specific heating of the nanoparticles and thus selective destruction of the cells to which the nanoparticles are bound.

In alternative embodiments, a DC magnetic field may be used. DC magnetic field uses less power than AC magnetic field and is commonly used in medical diagnostics. Use of DC magnetic field can induce magnetocytolysis and death of cells associated with the magnetic nanoparticles (e.g. cells which have internalised or bound to the nanoparticles). This causes cell death without hyperthermia, reducing the possibility of affecting surrounding tissue or healthy cells. A recent paper utilising a DC-based magnetic field has shown that ferric oxide-based nanoparticles coated with LH-RH (luteinizing-hormone releasing hormone) can provide cancer specific targetting in vitro, selectively killing cancer cells (Bergey E et al (2002) Biomed Microdevices 4, 293-9). Cells were exposed to a 7 tesla magnetic field to induce magnetolysis.

Nanoparticle size is also an important criterion in inducing magnetocytolysis on exposure to DC magnetic field. In general, larger particle sizes are required, in order to allow the nanoparticles to be physically oriented in the DC magnetic field.

Pharmaceutical Compositions

Aerosol Delivery

In a further aspect, the present invention provides the use of the nanoparticles described herein in aerosols. This is made possible by the small size of the nanoparticles. The aerosol compositions may be used to deliver antibacterials, in particular to the lungs for imaging and/or therapeutic use, e.g. in the treatment of conditions affecting the lungs.

Another advantage of the nanoparticles of the present invention is their exceptionally small size, which makes them more likely to be taken up by cells even when linked to targeting or therapeutic molecules.

The nanoparticles of the invention may be formulated as pharmaceutical compositions that may be in the forms of solid or liquid compositions. Such compositions will generally comprise a carrier of some sort, for example a solid carrier such as gelatine or an adjuvant or an inert diluent, or a liquid carrier such as water, petroleum, animal or vegetable oils, mineral oil or synthetic oil.

Physiological saline solution, or glycols such as ethylene glycol, propylene glycol or polyethylene glycol may be included. Such compositions and preparations generally contain at least 0.1 wt % of the compound.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Administration

The nanoparticle compositions may be administered to patients by any number of different routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 18th edition, Mack Publishing Company, Easton, Pa., 1990; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

EXAMPLES

Figure 1:
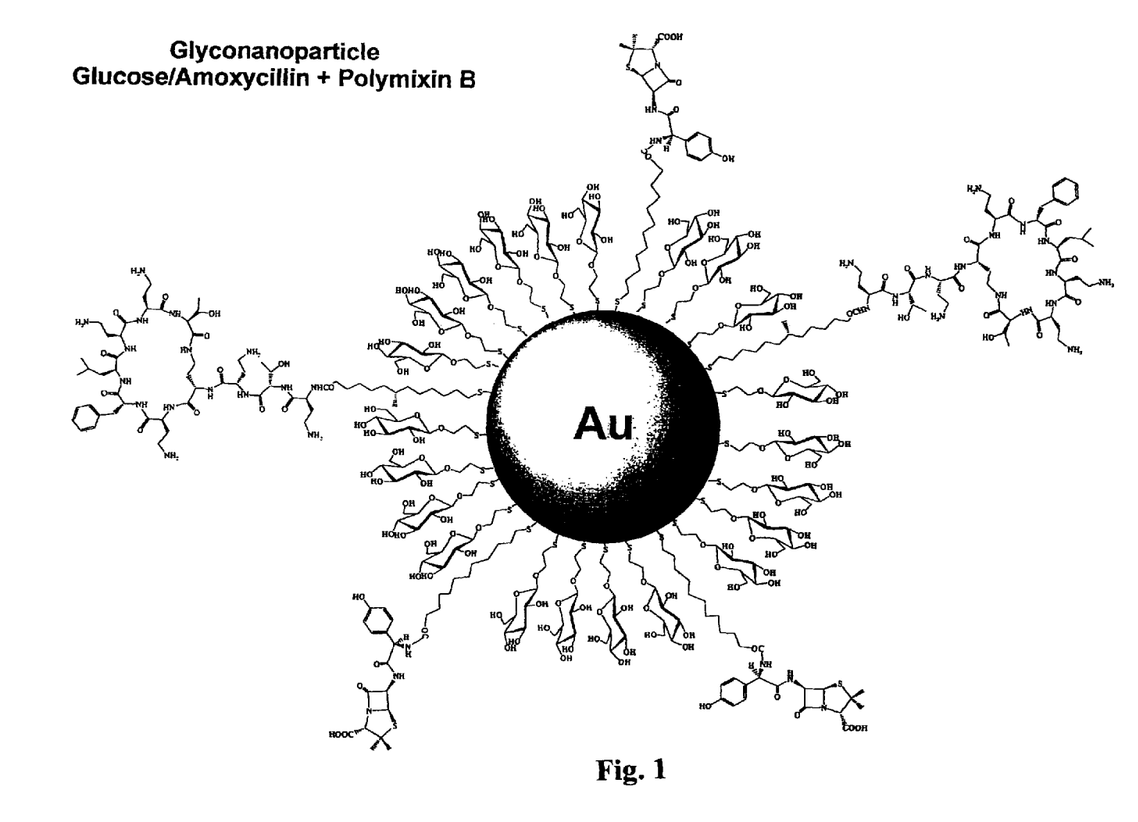
FIG. 1 shows a schematic representation of a preferred nanoparticle of the invention comprising glucose/amoxicillin and polymixin B ligands.
Figure 2:
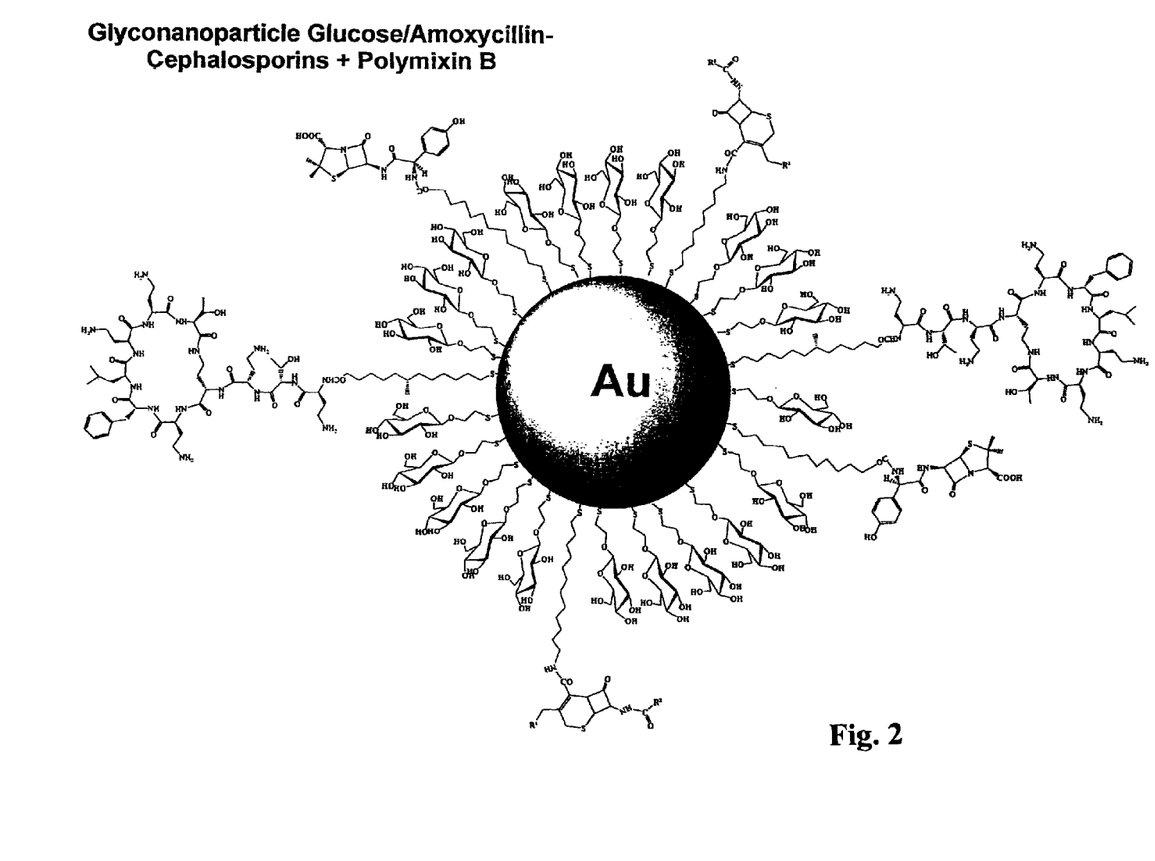
FIG. 2 shows a schematic representation of a preferred nanoparticle of the invention comprising glucose/amoxicillin-cephalosporins and polymixin B ligands.
Figure 3:
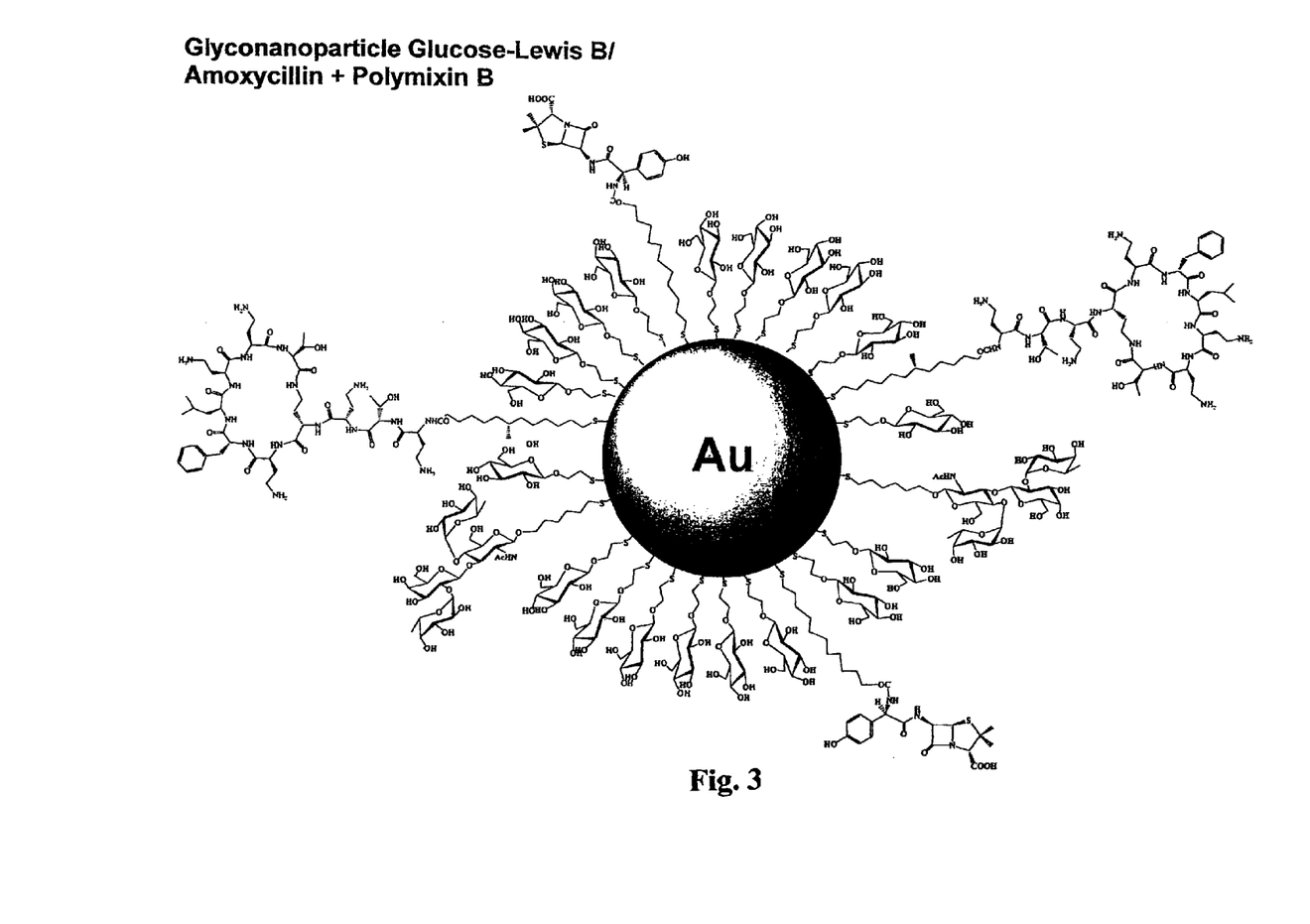
FIG. 3 shows a schematic representation of a preferred nanoparticle of the invention comprising glucose-Lewis B/amoxicillin and polymixin B ligands.
Figure 4A:
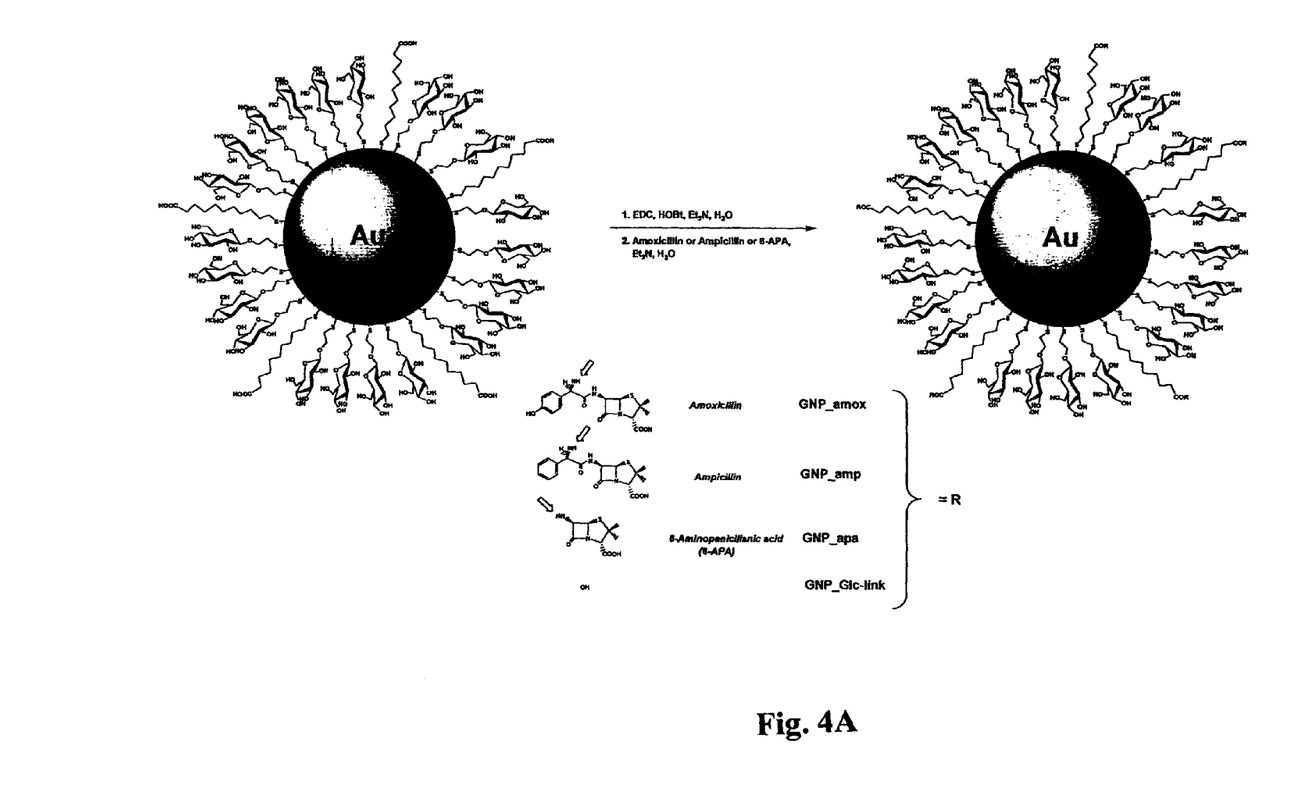
FIG. 4A-FIG. 4E shows the synthesis of the nanoparticles described in the experimental section, GNP_amox, GNP_amp, GNP_apa (FIG. 4A); GNP_GlcC5-LM91, GNP_GlcC5-LM41, GNP_GlcC5-LM21(FIG. 4B); GNP_Glc:Amoxicillin9:1 (FIG. 4C); GNP_Glc:Amoxicillin4:1 (FIG. 4D); and GNP_Glc:Amoxicillin2:1 (FIG. 4E).
Figure 4B:
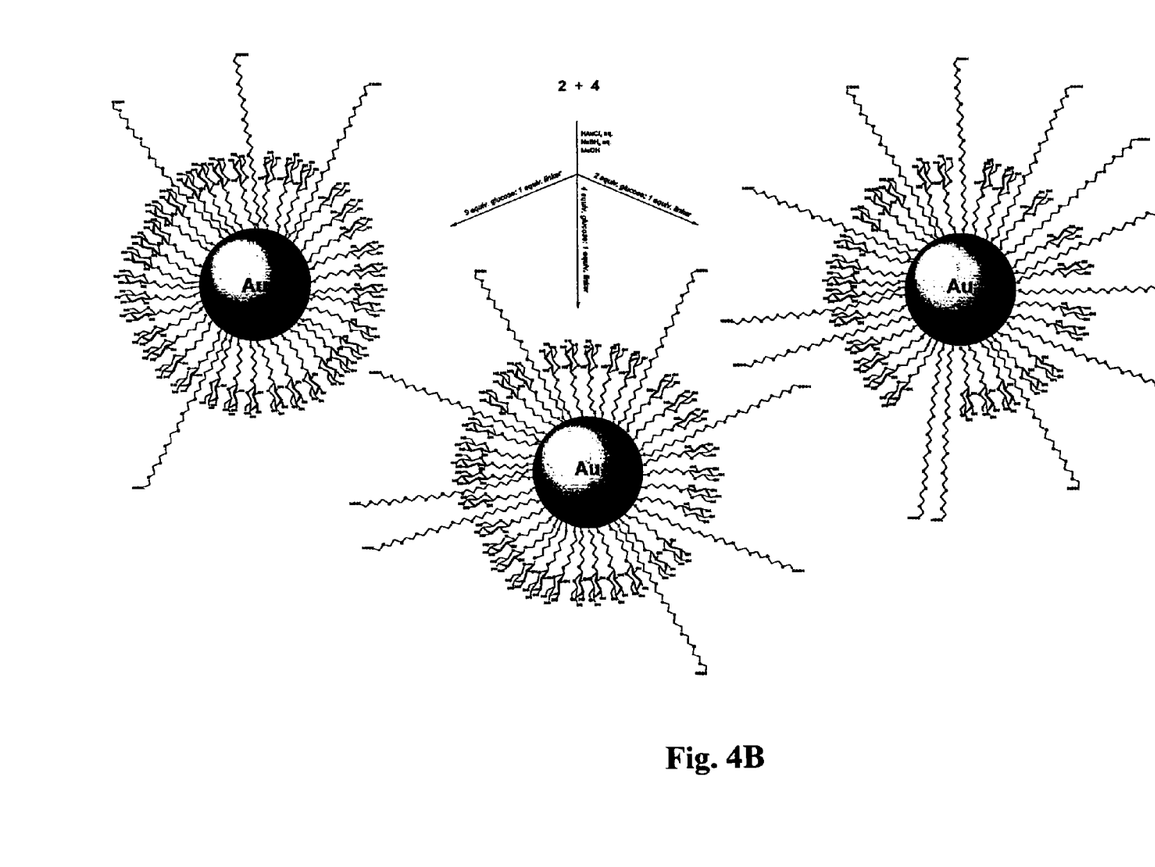
Figure 4C:
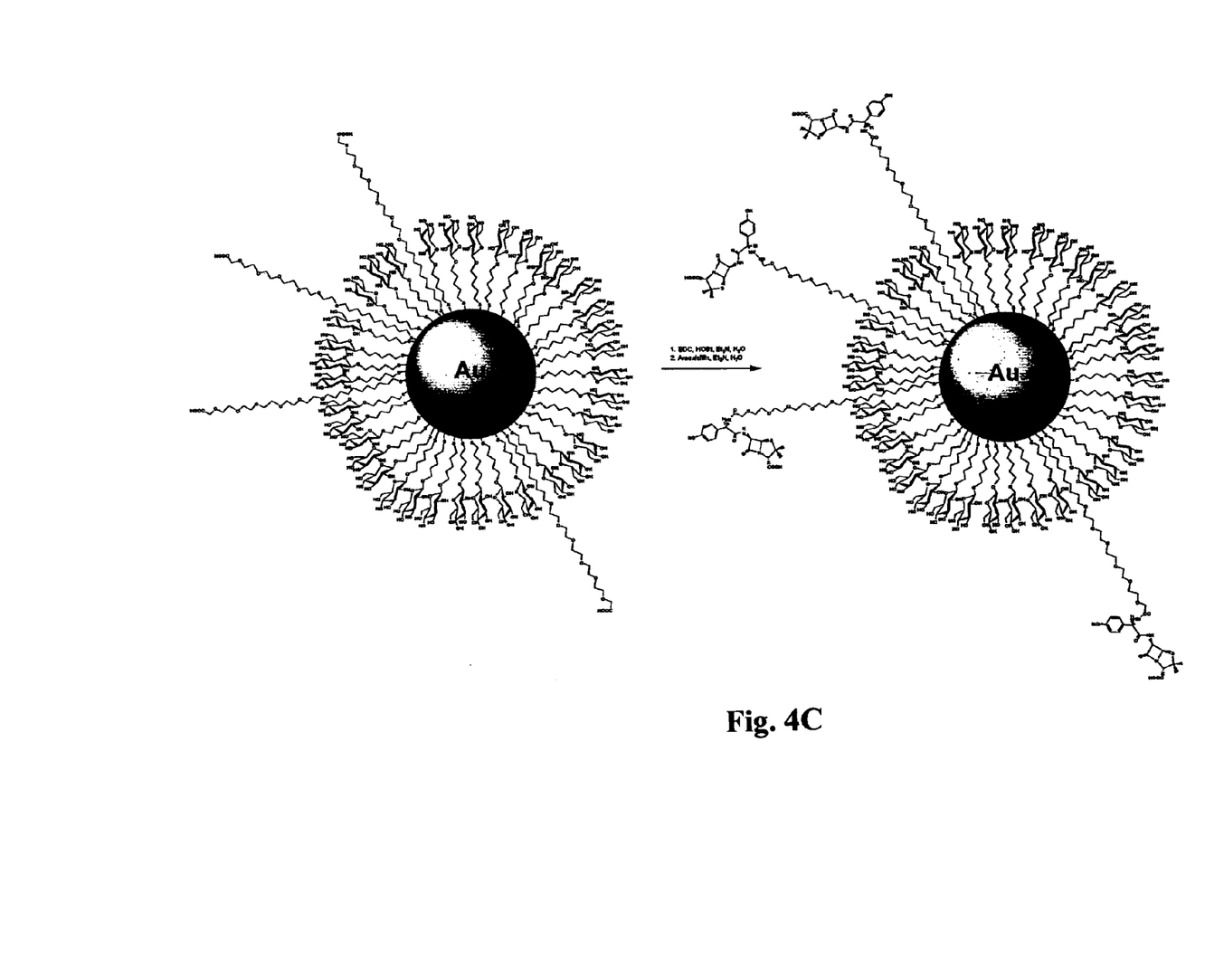
Figure 4D:
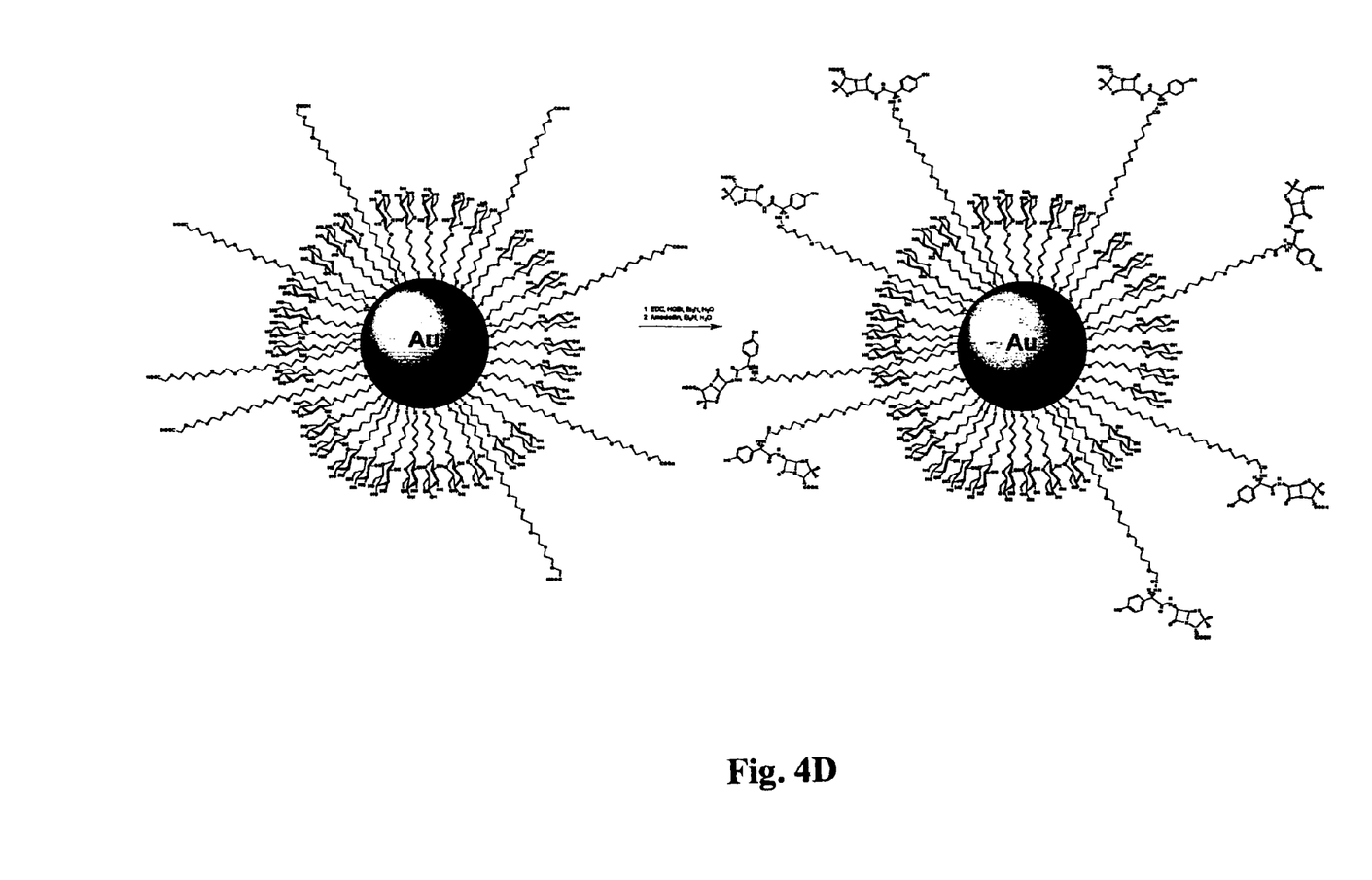
Figure 4E:
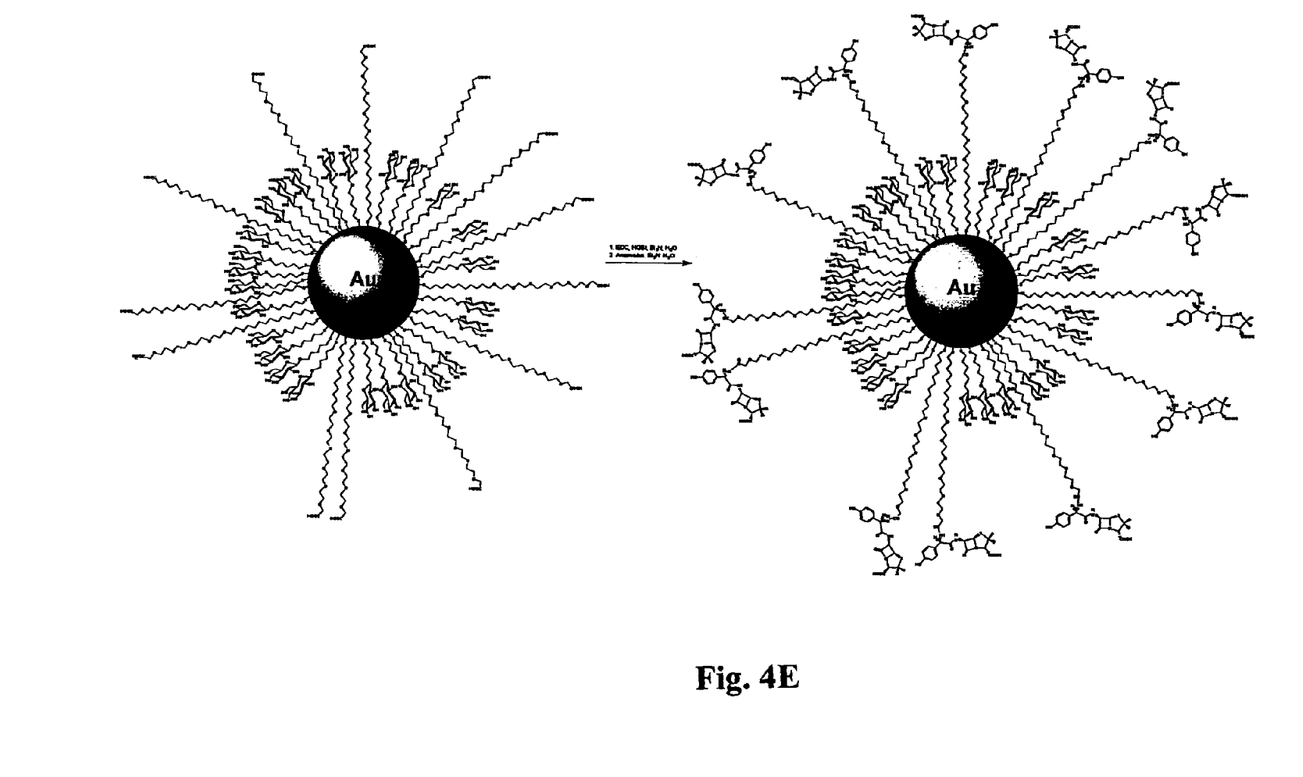

The nanoparticles shown in FIGS. 1 to 3 in which cores were conjugated to glucose-LewisB/amoxicillin/cephalosporins and polymixin B) ligands were synthesised according to protocols previously disclosed in WO 02/32404, WO 2004/108165 and the following papers: Luiz de Paz et al, Tetrahedron: Asymmetry, 16: 149-158, 2005, de la Fuente, Tetrahedron: Asymmetry, 13: 1879-1888, 2002 and de al Fuente, Glycoconjugate Journal, 21: 149-163, 2004.

Further examples of nanoparticles with antibiotic ligands were synthesised according to the following methods.

General Methods

Glucose derivatives 1 and 2 and Linker 4 was prepared following standard procedures. Linker 3, amoxicillin, ampicillin, 6-aminopenicillanic acid, N-(3-Dimethylaminopropyl)-N'-ethylcarbodiimide (EDC), 1-Hydroxybenzotriazole (HOBt), $Et_3N$, $HAuCl_4$, $NaBH_4$ were purchased from Aldrich Chemical Company. For all experiments and solutions, Nanopure water (18.1 mΩ) was used. In the following description, the ratios present in the names of some of the nanoparticles (e.g. Glc:Amoxicillin9:1) denote the molar ratio of the ligand components in the initial mixture. This ratio is generally retained in is kept in the GNP construct.

Preparation of Nanoparticles
a) GNP_Glc-link

To a solution of 1 (20 mg, 83.2 μmol) and 3 (6 mg, 27.5 μmol) in MeOH (9.1 mL), 0.025M aqueous solution of $HAuCl_4$ (1 mL, 25 μmol) was added. Then, 1N aqueous solution of $NaBH_4$ (500 μL, 500 μmol) was added in several portions with rapid shaking. The black suspension formed was shaken for an additional 2 h and the methanolic layer was separated by decantation. The black solid was dissolved in water (700 μL) and purified by centrifugal filtering (AMI- CON MW 10000, 30 min, 14000 rpm). The process was repeated twice, until the nanoparticles were free of salts and starting materials. The residue in the AMICON filters was dissolved in 1 mL of water and lyophilised to afford 6 mg of GNP_Glc-link. The successful lining of glucose ligands was confirmed by $^1$H-NMR (300 MHz, D$_2$O)

b) GNP-Activated

To a solution of GNP_Glc-link (4.5 mg) in H$_2$O (2 mL), HOBt (27 mg, 0.2 mmol), EDC (29 mg, 0.15 mmol) and Et$_3$N (50 μL, 0.36 mmol) were added. After stirring for 4 h, the reaction mixture was purified by centrifugal filtering (AMICON MW 10000, 30 min, 14000 rpm). The process was repeated twice, until the nanoparticles were free starting materials. The residue in the AMICON filters was dissolved in 4.5 mL of water and split into three portions (1.5 mL/each).

c) GNP_amox

To 1.5 mL of the above solution, amoxicillin (10 mg, 27 μmol) and Et$_3$N (15 μL, 108 μmol) were added. The reaction was stirred for 36 h. Then, the resulting mixture was purified by centrifugal filtering (AMICON MW 10000, 30 min, 14000 rpm). The process was repeated twice, until the nanoparticles were free starting materials. The residue in the AMICON filters was dissolved in 500 μL of water and lyophilised to afford 0.6 mg of GNP_amox. The successful linking of the amoxicillin ligands to the nanoparticles was confirmed using $^1$H-NMR (300 MHz, D$_2$O) by the presence of a peak for the antibiotic ligand in the 6.5-7.5 ppm zone. TEM: average diameter 1.5-2.5 nm.

d) GNP_amp

To 1.5 mL of the above solution, ampicillin (9.5 mg, 27 μmol) and Et$_3$N (15 μL, 108 μmol) were added. The reaction was stirred for 36 h. Then, the resulting mixture was purified by centrifugal filtering (AMICON MW 10000, 30 min, 14000 rpm). The process was repeated twice, until the nanoparticles were free starting materials. The residue in the AMICON filters was dissolved in 500 μL of water and lyophilised to afford 0.6 mg of GNP_amp. The successful linking of the ampicillin ligands to the nanoparticles was confirmed using $^1$H-NMR (300 MHz, D$_2$O) by the presence of a peak for the antibiotic ligand in the 7.0-7.5 ppm zone. TEM: average diameter 1.5-2.5 nm.

e) GNP_apa

To 1.5 mL of the above solution, 6-aminopenicillanic acid (6 mg, 27.7 μmol) and Et$_3$N (15 μL, 108 μmol) were added. The reaction was stirred for 36 h. Then, the resulting mixture was purified by centrifugal filtering (AMICON MW 10000, 30 min, 14000 rpm). The process was repeated twice, until the nanoparticles were free starting materials. The residue in the AMICON filters was dissolved in 500 μL of water and lyophilised to afford 0.6 mg of GNP_apa. TEM average diameter 1.5-2.5 nm.

f) GNP_GlcC5-LM91

To a solution of 2 (13.5 mg, 47.9 μmol) and 4 (2.8 mg, 5.3 μmol) in MeOH (4.4 mL), 0.025M aqueous solution of HAuCl$_4$ (525 μL, 13.1 μmol) was added. Then, 1N aqueous solution of NaBH$_4$ (262 μL, 262 μmol) was added in several portions with rapid shaking. The black suspension formed was shaken for an additional 2 h and the methanolic layer was separated by decantation. The black solid was dissolved in water (700 μL) and purified by centrifugal filtering (AMICON MW 10000, 30 min, 14000 rpm). The process was repeated twice, until the nanoparticles were free of salts and starting materials. The residue in the AMICON filters was dissolved in 1 mL of water and lyophilised to afford 3 mg of GNP_GlcC5-LM91. The identity of the product was confirmed by $^1$H-NMR (500 MHz, D$_2$O). TEM: average diameter 1.5-2.5 nm.

g) GNP_Glc:Amoxicillin9:1

To a solution of GNP_GlcC5-LM91 (3 mg) in H$_2$O (2 mL), HOBt (13 mg, 96.2 μmol), EDC (14 mg, 73 μmol) and Et$_3$N (20 μL, 144 μmol) were added. After stirring for 3 h, the reaction mixture was purified by centrifugal filtering (AMICON MW 10000, 30 min, 14000 rpm). The process was repeated twice, until the nanoparticles were free starting materials. The residue in the AMICON filters was dissolved in 2 mL of water and used directly for the following reaction. Amoxicillin (6 mg, 16.4 μmol) and Et$_3$N (8 μL, 57.6 μmol) were added to this solution and the reaction was stirred for 24 h. Then, the resulting mixture was purified by centrifugal filtering (AMICON MW 10000, 30 min, 14000 rpm). The process was repeated twice, until the nanoparticles were free starting materials. The residue in the AMICON filters was dissolved in 500 μL of water and lyophilised to afford 1.8 mg of GNP Glc:Amoxicillin9:1. The successful linking of the amoxicillin ligands to the nanoparticles was confirmed using $^1$H-NMR (300 MHz, D$_2$O) by the presence of a peak for the antibiotic ligand in the 6.5-7.5 ppm zone. TEM: average diameter 1.8-2.5 nm. See FIG. 11.

h) GNP_GlcC5-LM41

To a solution of 2 (12 mg, 42.5 μmol) and 4 (5.5 mg, 10.4 μmol) in MeOH (4.4 mL), 0.025M aqueous solution of HAuCl$_4$ (525 μL, 13.1 μmol) was added. Then, 1N aqueous solution of NaBH$_4$ (262 μL, 262 μmol) was added in several portions with rapid shaking. The black suspension formed was shaken for an additional 2 h and the methanolic layer was separated by decantation. The black solid was dissolved in water (700 μL) and purified by centrifugal filtering (AMICON MW 10000, 30 min, 14000 rpm). The process was repeated twice, until the nanoparticles were free of salts and starting materials. The residue in the AMICON filters was dissolved in 1 mL of water and lyophilised to afford 3.1 mg of GNP_GlcC5-LM41. The identity of the product was confirmed by $^1$H-NMR (500 MHz, D$_2$O). TEM: average diameter 1.8-2.5 nm.

i) GNP Glc:Amoxicillin4:1

To a solution of GNP_GlcC5-LM41 (3.1 mg) in H$_2$O (2 mL), HOBt (20 mg, 148 μmol), EDC (21 mg, 109.5 mmol) and Et$_3$N (30 μL, 216 μmol) were added. After stirring for 3 h, the reaction mixture was purified by centrifugal filtering (AMICON MW 10000, 30 min, 14000 rpm). The process was repeated twice, until the nanoparticles were free starting materials. The residue in the AMICON filters was dissolved in 2 mL of water and used directly for the following reaction. Amoxicillin (10 mg, 27.4 μmol) and Et$_3$N (14 μL, 100.8 μmol) were added to this solution and the reaction was stirred for 24 h. Then, the resulting mixture was purified by centrifugal filtering (AMICON MW 10000, 30 min, 14000 rpm). The process was repeated twice, until the nanoparticles were free of starting materials. The residue in the AMICON filters was dissolved in 500 μL of water and lyophilised to afford 2.0 mg of GNP Glc:Amoxicillin4:1. The successful linking of the amoxicillin ligands to the nanoparticles was confirmed using $^1$H-NMR (300 MHz, D$_2$O) by the presence of a peak for the antibiotic ligand in the 6.5-7.5 ppm zone. TEM average diameter 1.4-2.2 nm.

j) GNP_GlcC5-LM21

To a solution of 2 (10 mg, 35.4 mol) and 4 (9 mg, 17.1 μmol) in MeOH (4.4 mL), 0.025M aqueous solution of HAuCl$_4$ (525 μL, 13.1 μmol) was added. Then, 1N aqueous solution of NaBH$_4$ (262 μL, 262 μmol) was added in several portions with rapid shaking. The black suspension formed was shaken for an additional 2 h and the methanolic layer was separated by decantation. The black solid was dissolved in water (700 μL) and purified by centrifugal filtering (AMI- CON MW 10000, 30 min, 14000 rpm). The process was repeated twice, until the nanoparticles were free of salts and starting materials. The residue in the AMICON filters was dissolved in 1 mL of water and lyophilised to afford 2.8 mg of GNP_GlcC5-LM21. The identity of the product was confirmed by $^1$H-NMR (500 MHz, D$_2$O). TEM: average diameter 1.8-2.5 nm.

k) GNP Glc:Amoxicillin9:1

To a solution of GNP_GlcC5-LM91 (2.8 mg) in H$_2$O (2 mL), HOBt (26 mg, 192.4 μmol), EDC (28 mg, 146 μmol) and Et$_3$N (40 μL, 288 μmol) were added. After stirring for 3 h, the reaction mixture was purified by centrifugal filtering (AMICON MW 10000, 30 min, 14000 rpm). The process was repeated twice, until the nanoparticles were free starting materials. The residue in the AMICON filters was dissolved in 2 mL of water and used directly for the following reaction. Amoxicillin (14 mg, 38.3 μmol) and Et$_3$N (20 μL, 144 μmol) were added to this solution and the reaction was stirred for 24 h. Then, the resulting mixture was purified by centrifugal filtering (AMICON MW 10000, 30 min, 14000 rpm). The process was repeated twice, until the nanoparticles were free starting materials. The residue in the AMICON filters was dissolved in 500 μL of water and lyophilised to afford 1.4 mg of GNP Glc:Amoxicillin2:1. The successful linking of the amoxicillin ligands to the nanoparticles was confirmed using $^1$H-NMR (300 MHz, D$_2$O) by the presence of a peak for the antibiotic ligand in the 6.5-7.5 ppm zone. TEM: average diameter 2.0-2.7 nm.

The references cited herein are all expressly incorporated by reference in their entirety.

The invention claimed is:

1. A nanoparticle which comprises a core including metal atoms, said core being covalently linked via linker groups to a plurality of ligands which comprise at least:
    (a) a first species of ligand comprising an antibiotic linked to said core via a first linker group; and
    (b) a second species of ligand comprising a carbohydrate linked to said core via a second linker group,
        wherein (a) and (b) are different, and wherein said first linker group is longer than said second linker group and is selected from the group consisting of:
    HOOC—(CH$_2$)$_{10}$—SH; and
    HOOC—(CH$_2$—O—CH$_2$)$_7$—(CH$_2$)$_{10}$—SH.

2. The nanoparticle of claim 1, wherein the core is magnetic.

3. The nanoparticle of claim 1, further comprising an antibacterial ligand that binds a bacterial marker, said antibacterial ligand being selected from the group consisting of antibodies and lectins.

4. The nanoparticle of claim 3, wherein the bacterial marker is a carbohydrate marker.

5. The nanoparticle of claim 1, wherein the core of the nanoparticle has a mean diameter between 0.5 and 10 nm.

6. The nanoparticle of claim 1, wherein the nanoparticle including its ligands has a mean diameter between 10 and 30 nm.

7. The nanoparticle of claim 1, wherein the core comprises Au, Pd or Fe.

8. The nanoparticle of claim 7, wherein the core is an alloy selected from Au/Fe, Au/Ag, Au/Cu, Au/Ag/Cu, Au/Pt, Au/Pd, Au/Ag/Cu/Pd, Au/Cu, Au/Gd, Au/Fe/Cu, Au/Fe/Gd or Au/Fe/Cu/Gd.

9. The nanoparticle of claim 1, wherein the nanoparticle comprises passive metal atoms and magnetic metal atoms in the core in a ratio between 5:0.1 and 2:5.

10. The nanoparticle of claim 9, wherein the passive metal is gold, platinum, silver or copper, and the magnetic metal is iron or cobalt.

11. The nanoparticle of claim 1, wherein the nanoparticle comprises a label.

12. The nanoparticle of claim 11, wherein the label is a fluorescent group, a radionuclide, a magnetic label or a dye.

13. The nanoparticle of claim 12, wherein the magnetic label is a paramagnetic group comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ or lanthanides$^{+3}$.

14. The nanoparticle of claim 1, wherein the nanoparticle is water soluble.

15. The nanoparticle of claim 1, wherein the ligands further comprise one or more peptides, a protein domain, a nucleic acid molecule, a lipidic group, a carbohydrate group, any organic or anionic or cationic group, a glycolipid or a glycoprotein.

16. The nanoparticle of claim 1, wherein the ligands comprise one or more glycoconjugates to form glyconanoparticles.

17. A composition comprising a population of one or more of the nanoparticles of claim 1.

18. The nanoparticle of claim 1, wherein the plurality of ligands comprises more than one antibiotic.

19. The nanoparticle of claim 1, wherein said second linker group comprises a C2 to C5 alkyl chain.

20. The nanoparticle of claim 1, wherein said second linker group is selected from the group consisting of:
    HO—(CH$_2$)$_2$—SH; and
    HO—(CH$_2$)$_5$—SH.

* * * * *